United States Patent
Moradi et al.

(10) Patent No.: US 11,653,951 B2
(45) Date of Patent: May 23, 2023

(54) EXTERNAL ORTHOPEDIC FIXATION DEVICE

(71) Applicants: Ali Moradi, Mashhad (IR); Morteza Moradi, Tehran (IR); Ehsan Vahedi, Mashhad (IR); Saeed Kermani, Mashhad (IR); Mohammad Hossein Ebrahimzadeh, Mashhad (IR); Nahid Mojaver, Mashhad (IR); Fatemeh Salehi, Mashhad (IR)

(72) Inventors: Ali Moradi, Mashhad (IR); Morteza Moradi, Tehran (IR); Ehsan Vahedi, Mashhad (IR); Saeed Kermani, Mashhad (IR); Mohammad Hossein Ebrahimzadeh, Mashhad (IR); Nahid Mojaver, Mashhad (IR); Fatemeh Salehi, Mashhad (IR)

(*) Notice: Subject to any disclaimer, the term of this patent is extended or adjusted under 35 U.S.C. 154(b) by 655 days.

(21) Appl. No.: 16/675,241

(22) Filed: Nov. 6, 2019

(65) Prior Publication Data

US 2020/0069334 A1     Mar. 5, 2020

Related U.S. Application Data

(60) Provisional application No. 62/756,089, filed on Nov. 6, 2018.

(51) Int. Cl.
*A61B 17/64* (2006.01)
*A61B 17/88* (2006.01)
*A61B 17/60* (2006.01)

(52) U.S. Cl.
CPC ...... *A61B 17/6425* (2013.01); *A61B 17/8869* (2013.01); *A61B 2017/606* (2013.01)

(58) Field of Classification Search
CPC ......... A61B 17/56; A61B 17/60; A61B 17/64; A61B 17/6425; A61B 17/6433; A61B 17/6466; A61B 17/6483; A61B 17/6491; A61B 17/66; A61B 2017/564; A61B 2017/567; A61B 2017/568; A61B 2017/606
See application file for complete search history.

(56) References Cited

U.S. PATENT DOCUMENTS

| | | | | |
|---|---|---|---|---|
| 2,238,870 A * | 4/1941 | Haynes | .................. | A61B 17/66 403/56 |
| 2,251,209 A * | 7/1941 | Stader | .................... | A61B 17/60 174/138 R |
| 2,391,537 A * | 12/1945 | Anderson | .............. | A61B 17/66 606/59 |
| 3,961,854 A * | 6/1976 | Jaquet | ....................... | F16B 2/12 403/68 |

(Continued)

*Primary Examiner* — Lynnsy M Summitt
(74) *Attorney, Agent, or Firm* — Bajwa IP Law Firm; Haris Zaheer Bajwa

(57) ABSTRACT

An external orthopedic fixation device. The external orthopedic device includes a radius fixing member, a metacarpus fixing member, and a coupling member. The radius fixing member is configured to be secured to a radius bone of a patient. The metacarpus fixing member is configured to be secured to a metacarpus bone of the patient. The coupling member is disposed between the radius fixing member and the metacarpus fixing member. The coupling member is configured to connect the radius fixing member and the metacarpus fixing member.

14 Claims, 14 Drawing Sheets

(56) References Cited

U.S. PATENT DOCUMENTS

| | | | | |
|---|---|---|---|---|
| 4,187,841 A | * | 2/1980 | Knutson | A61B 17/66 606/57 |
| 4,456,004 A | * | 6/1984 | Kenny | A61B 17/6441 606/57 |
| 4,548,199 A | * | 10/1985 | Agee | A61B 17/6425 606/57 |
| 4,611,586 A | * | 9/1986 | Agee | A61B 17/6425 606/57 |
| 4,621,627 A | * | 11/1986 | DeBastiani | A61B 17/66 606/57 |
| 4,628,919 A | * | 12/1986 | Clyburn | A61B 17/6425 606/57 |
| 4,730,608 A | * | 3/1988 | Schlein | A61B 17/66 606/57 |
| 4,919,119 A | * | 4/1990 | Jonsson | A61B 17/6425 606/54 |
| 4,922,896 A | * | 5/1990 | Agee | A61B 17/6425 606/57 |
| 4,988,349 A | * | 1/1991 | Pennig | A61B 17/66 606/57 |
| 5,019,077 A | * | 5/1991 | De Bastiani | A61B 17/6416 606/57 |
| 5,026,372 A | * | 6/1991 | Sturtzkopf | A61B 17/6458 606/54 |
| 5,108,394 A | * | 4/1992 | Kurokawa | A61B 17/6458 606/59 |
| 5,122,140 A | * | 6/1992 | Asche | A61B 17/6425 606/57 |
| 5,207,676 A | * | 5/1993 | Canadell | A61B 17/6491 606/57 |
| 5,275,599 A | * | 1/1994 | Zbikowski | A61B 17/6491 606/53 |
| 5,304,177 A | * | 4/1994 | Pennig | A61B 17/6466 403/396 |
| 5,320,622 A | * | 6/1994 | Faccioli | A61B 17/6491 606/58 |
| 5,391,167 A | * | 2/1995 | Pong | A61B 17/6425 606/57 |
| 5,429,637 A | * | 7/1995 | Hardy | A61B 17/6425 606/54 |
| 5,437,666 A | * | 8/1995 | Tepic | A61B 17/6425 606/54 |
| 5,437,667 A | * | 8/1995 | Papierski | A61B 17/6425 606/55 |
| 5,443,465 A | * | 8/1995 | Pennig | G01N 30/96 606/301 |
| 5,468,241 A | * | 11/1995 | Metz-Stavenhagen | F16B 7/06 606/319 |
| 5,545,162 A | * | 8/1996 | Huebner | A61B 17/60 606/57 |
| 5,620,442 A | * | 4/1997 | Bailey | A61B 17/6416 606/57 |
| 5,658,283 A | * | 8/1997 | Huebner | A61B 17/7291 606/62 |
| 5,662,648 A | * | 9/1997 | Faccioli | A61B 17/6458 606/53 |
| 5,662,649 A | * | 9/1997 | Huebner | A61B 17/60 606/57 |
| 5,707,370 A | * | 1/1998 | Berki | A61B 17/6425 606/55 |
| 5,743,898 A | * | 4/1998 | Bailey | A61B 17/171 606/57 |
| 5,788,695 A | * | 8/1998 | Richardson | A61B 17/6491 606/57 |
| 5,803,924 A | * | 9/1998 | Oni | A61B 17/6416 606/57 |
| 5,855,580 A | * | 1/1999 | Kreidler | A61B 17/663 606/904 |
| 5,941,877 A | * | 8/1999 | Viegas | A61B 17/6425 606/54 |
| 5,951,556 A | * | 9/1999 | Faccioli | A61B 17/66 606/65 |
| 5,976,134 A | * | 11/1999 | Huebner | A61B 17/60 606/62 |
| 6,010,501 A | * | 1/2000 | Raskin | A61B 17/6425 606/54 |
| 6,056,748 A | * | 5/2000 | Weiner | A61B 17/6425 606/54 |
| 6,162,223 A | * | 12/2000 | Orsak | A61B 17/6425 606/59 |
| 6,162,224 A | * | 12/2000 | Huebner | A61B 17/6458 606/59 |
| 6,171,308 B1 | * | 1/2001 | Bailey | A61B 17/60 606/54 |
| 6,171,309 B1 | * | 1/2001 | Huebner | A61B 17/6416 606/57 |
| 6,176,860 B1 | * | 1/2001 | Howard | A61B 17/6491 606/57 |
| 6,245,071 B1 | * | 6/2001 | Pierson | A61B 17/66 606/57 |
| 6,428,540 B1 | * | 8/2002 | Claes | A61B 17/66 606/53 |
| 6,500,177 B1 | * | 12/2002 | Martinelli | A61B 17/6458 606/57 |
| 6,652,524 B1 | * | 11/2003 | Weiner | A61B 17/6425 606/59 |
| 6,709,433 B1 | * | 3/2004 | Schoenefeld | A61B 17/6425 606/57 |
| 8,574,232 B1 | * | 11/2013 | Ross | A61B 17/66 606/57 |
| 10,980,655 B1 | * | 4/2021 | Marin | A61F 5/0127 |
| 11,166,750 B1 | * | 11/2021 | Wurapa | A61B 17/6416 |
| 11,241,263 B1 | * | 2/2022 | Nordt, III | A61B 17/8023 |
| 2002/0115998 A1 | * | 8/2002 | Schoenefeld | A61B 17/6466 606/55 |
| 2002/0169447 A1 | * | 11/2002 | Agee | A61B 17/6425 606/60 |
| 2003/0055425 A1 | * | 3/2003 | Hajianpour | A61B 17/60 606/57 |
| 2003/0069580 A1 | * | 4/2003 | Langmaid | A61B 17/6458 606/59 |
| 2003/0225406 A1 | * | 12/2003 | Weiner | A61B 17/6425 606/54 |
| 2003/0225407 A1 | * | 12/2003 | Estrada, Jr. | A61B 17/6425 606/54 |
| 2004/0059331 A1 | * | 3/2004 | Mullaney | A61B 17/6458 606/59 |
| 2004/0097944 A1 | * | 5/2004 | Koman | A61B 17/6425 606/55 |
| 2004/0181221 A1 | * | 9/2004 | Huebner | A61B 17/6425 606/59 |
| 2004/0249375 A1 | * | 12/2004 | Agee | A61B 17/6425 606/54 |
| 2006/0015118 A1 | * | 1/2006 | Richter | A61B 17/66 606/90 |
| 2006/0235383 A1 | * | 10/2006 | Hollawell | A61B 17/6416 606/54 |
| 2007/0043354 A1 | * | 2/2007 | Koo | A61B 17/66 606/58 |
| 2007/0161984 A1 | * | 7/2007 | Cresina | A61B 17/6425 606/54 |
| 2007/0173837 A1 | * | 7/2007 | Chan | A61B 17/66 606/63 |
| 2008/0275509 A1 | * | 11/2008 | Clifford | A61B 17/68 606/301 |
| 2008/0275563 A1 | * | 11/2008 | Makower | A61B 17/68 623/20.21 |
| 2008/0275567 A1 | * | 11/2008 | Makower | A61B 17/8004 623/23.41 |
| 2009/0036892 A1 | * | 2/2009 | Karidis | A61B 17/66 606/60 |
| 2009/0093890 A1 | * | 4/2009 | Gelbart | A61B 17/7062 623/24 |
| 2009/0118733 A1 | * | 5/2009 | Orsak | A61B 17/6475 606/329 |
| 2009/0228006 A1 | * | 9/2009 | Mussolin | A61B 17/6416 606/59 |

(56) References Cited

U.S. PATENT DOCUMENTS

| | | | |
|---|---|---|---|
| 2010/0076434 A1* | 3/2010 | Hajianpour | A61B 17/66 606/54 |
| 2010/0076436 A1* | 3/2010 | Hajianpour | A61B 17/6491 606/59 |
| 2010/0222778 A1* | 9/2010 | Bagnasco | A61B 17/66 606/58 |
| 2011/0172662 A1* | 7/2011 | Keilen | A61B 17/68 606/57 |
| 2012/0095462 A1* | 4/2012 | Miller | A61B 17/6466 29/428 |
| 2012/0150180 A1* | 6/2012 | Verma | A61B 17/66 606/59 |
| 2012/0209266 A1* | 8/2012 | Ottoboni | A61B 17/6425 606/54 |
| 2012/0253410 A1* | 10/2012 | Taylor | A61B 17/6458 606/86 R |
| 2012/0259344 A1* | 10/2012 | Johnston, Jr. | A61B 17/8004 606/105 |
| 2013/0013067 A1* | 1/2013 | Landry | A61B 17/683 623/14.12 |
| 2013/0110110 A1* | 5/2013 | Waisman | A61B 17/6458 606/59 |
| 2014/0276817 A1* | 9/2014 | Murray | A61B 17/62 606/56 |
| 2014/0276821 A1* | 9/2014 | Murray | A61B 17/62 606/57 |
| 2014/0276824 A1* | 9/2014 | Cresina | A61B 17/66 606/59 |
| 2015/0038966 A1* | 2/2015 | Zandona | A61B 17/64 606/59 |
| 2015/0272644 A1* | 10/2015 | Noon | A61B 17/66 606/90 |
| 2015/0366587 A1* | 12/2015 | Van Dyke | A61B 17/66 606/57 |
| 2015/0369223 A1* | 12/2015 | Hallila | F03G 7/065 60/527 |
| 2016/0022314 A1* | 1/2016 | Bordeaux | A61B 17/60 606/56 |
| 2017/0071633 A1* | 3/2017 | Sanders | A61B 17/6458 |
| 2017/0209177 A1* | 7/2017 | Kachooei | A61B 17/6458 |
| 2018/0028235 A1* | 2/2018 | Simpson | A61B 17/7025 |
| 2018/0228515 A1* | 8/2018 | Ross | A61B 17/6491 |
| 2018/0296246 A1* | 10/2018 | Perret | A61B 17/6441 |
| 2019/0269438 A1* | 9/2019 | Simpson | A61B 17/7037 |
| 2019/0282274 A1* | 9/2019 | Singh | A61B 17/645 |
| 2019/0388121 A1* | 12/2019 | Struik | A61B 17/64 |
| 2020/0000492 A1* | 1/2020 | Samchukov | A61B 17/66 |
| 2020/0375628 A1* | 12/2020 | Foo | A61B 17/6425 |
| 2021/0100714 A1* | 4/2021 | Marin | A61B 17/6433 |
| 2021/0228239 A1* | 7/2021 | Sanders | A61B 17/6416 |

* cited by examiner

300

302

322

304

342

300

EXTERNAL ORTHOPEDIC FIXATION DEVICE

CROSS-REFERENCE TO RELATED APPLICATION

This application claims the benefit of priority from U.S. Provisional Patent Application Ser. No. 62/756,089, filed on Nov. 6, 2018, and entitled "DYNAMIC DISTAL RADIUS EXTERNAL FIXATOR EXERTING PRECISE FORCE PERPENDICULAR TO FRACTURE SURFACE" which is incorporated herein by reference in its entirety.

TECHNICAL FIELD

The present disclosure generally relates to orthopedics, and particularly to orthopedic devices, and more particularly, to an external orthopedic fixation device for repairing fractures and dislocations of a distal radius of a patient.

BACKGROUND

Colle's fracture and distal radius fracture are common injuries among adults, including middle-aged to elderly individuals who suffer from osteoporosis as well as younger adults who suffer falls during sports, motor vehicle accidents, or other vigorous activities. A colle's fracture is a fracture of a radius, i.e., a forearm bone on a thumb side. A distal radius fracture typically occurs when one begins to fall and extends one's hand as a reflex to lessen a force of hitting the ground. The fall may produce a sudden impact of a body weight on a heel of a hand which may result in a fracture of a radius bone just above a wrist joint with or without an associated wrist joint injury.

Realignment and setting of bones crushed by a Colle's fracture or a distal radius fracture are typically performed with an aid of an external fixator or fixation device, which may be a mechanically adjustable splint that may be mounted externally to a forearm and a hand through percutaneous pins or screws that may secure the device to bones on either side of a fracture site. External fixators may be designed in such a way that permit initial alignment of a fracture fragments and then stabilize fragments and damaged soft tissue as they heal. Furthermore, external fixators may be designed in such a way that provides a facility for a surgeon to allow him/her to exert a tensile force to a radius bone of a patient. In order to heal a Colle's fracture or a distal radius fracture, a controllable tensile force may be needed to be applied to a radius bone along an axis perpendicular to a fracture surface. But, typical external fixators or fixation devices fail to provide a facility for a surgeon to allow him/her to exert a controllable tensile force along an axis perpendicular to a fracture surface. There is, therefore, a need for an external fixator that enables a surgeon to achieve alignment of a fracture and also apply a controllable tensile force to a radius bone along an axis perpendicular to a fracture surface.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary external orthopedic device. An exemplary external orthopedic device may include a radius fixing member, a metacarpus fixing member, and a coupling member. In an exemplary embodiment, the radius fixing member may be configured to be secured to a radius bone of a patient. In an exemplary embodiment, the metacarpus fixing member may be configured to be secured to a metacarpus bone of the patient.

In an exemplary embodiment, the coupling member may be disposed between the radius fixing member and the metacarpus fixing member. In an exemplary embodiment, the coupling member may be configured to connect the radius fixing member and the metacarpus fixing member.

In an exemplary embodiment, the coupling member may include a radius coupling element, and a metacarpus coupling element. In an exemplary embodiment, the radius coupling element may be disposed between the metacarpus fixing member and the radius coupling element. In an exemplary embodiment, the metacarpus coupling element may be connected to the metacarpus fixing member and the radius coupling element.

In an exemplary embodiment, the metacarpus coupling element may be configured to rotate around a second axis. In an exemplary embodiment, the second axis may be fixed to the radius coupling element. In an exemplary embodiment, the coupling member may be configured to allow rotational movements of the radius fixing member around the first axis and the second axis.

In an exemplary embodiment, the metacarpus fixing member may include an adjusting hole. In an exemplary embodiment, the metacarpus coupling element may include a first adjusting rod associated with the adjusting hole, the first adjusting rod disposed slidably inside a first side of the adjusting hole.

In an exemplary embodiment, a distance between the radius fixing member and the metacarpus fixing member may be configured to be changed responsive to linear movement of the first adjusting rod inside the adjusting hole and along a third axis.

In an exemplary embodiment, the external orthopedic fixation device may further include a force adjusting mechanism configured to exert a tensile force between the radius fixing member and the metacarpus fixing member through urging the first adjusting rod to move linearly inside the adjusting hole and along the third axis.

In an exemplary embodiment, the force adjusting mechanism may include a second adjusting rod including a second hollow cylindrical section. In an exemplary embodiment, the second adjusting rod may be configured to be inserted inside a second side of the adjusting hole and also may be configured to urge the first adjusting rod to move linearly inside the adjusting hole and along the third axis.

In an exemplary embodiment, the force adjusting mechanism may further include a pushing member and a spring. In an exemplary embodiment, the pushing member may include a first hollow cylindrical section. In an exemplary embodiment, the first hollow cylindrical section may be disposed slidably inside the second hollow cylindrical section. In an exemplary embodiment, the spring may be disposed between the second adjusting rod and the pushing member. In an exemplary embodiment, the spring may be disposed inside the first hollow cylindrical section and the second hollow cylindrical section.

In an exemplary embodiment, responsive to linear movement of the pushing member inside the second hollow cylindrical section and along a fourth axis, the spring may be configured to compress, and to thereby, urge the second adjusting rod to move along the fourth axis.

In an exemplary embodiment, the force adjusting mechanism may further include a shell. In an exemplary embodiment, the second adjusting rod and the pushing member may be disposed slidably inside the shell. In an exemplary embodiment, responsive to linear movement of the first hollow cylindrical section of pushing member inside the second hollow cylindrical section and along the fourth axis, the spring may be configured to compress, and to thereby urge the second adjusting rod to move along the fourth axis and inside the shell.

In an exemplary embodiment, the first axis may be perpendicular to the second axis. In an exemplary embodiment, the second axis may be perpendicular to the third axis. In an exemplary embodiment, the fourth axis may be the same as the third axis.

In an exemplary embodiment, the shell may include a slot on an outermost surface of the shell. In an exemplary embodiment, the slot may be configured to provide a view of the pushing member and the second adjusting rod to a surgeon.

In an exemplary embodiment, the coupling member may further include a first locking nut and a second locking nut. In an exemplary embodiment, a first internally threaded section of the first locking nut may correspond to a first externally threaded section of the first attaching rod. In an exemplary embodiment, the first internally threaded section of the first locking nut may be configured to be meshed with the first externally threaded section of the first attaching rod.

In an exemplary embodiment, responsive to fastening the first locking nut onto the first attaching rod, the radius coupling element may be configured to be prevented from rotating around the first axis and, to thereby, radius coupling element may be fixed relative to radius fixing member.

In an exemplary embodiment, a second internally threaded section of the second locking nut may correspond to a second externally threaded section of the second attaching rod. In an exemplary embodiment, the second internally threaded section of the second locking nut may be configured to be meshed with the second externally threaded section of the second attaching rod.

In an exemplary embodiment, responsive to fastening the second locking nut onto the second attaching rod, the metacarpus coupling element may be configured to be prevented from rotating around the second axis and, to thereby, metacarpus coupling element may be fixed relative to radius coupling element.

In an exemplary embodiment, the coupling member may further include a locking screw associated with the first adjusting rod. In an exemplary embodiment, responsive to fastening the locking screw, a friction between the locking screw and the first adjusting rod may be configured to be increased, and to thereby, prevent first adjusting rod from linear movement along the third axis, and to thereby, fix the metacarpus coupling element relative to metacarpus fixing member.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Herein is disclosed an exemplary orthopedic device for repairing fractures and dislocations of a fractured distal radius of a patient. An exemplary orthopedic device may include a radius fixing member and a metacarpus fixing member. The radius fixing member may be secured to a radius of a patient and the metacarpus fixing member may be secured to a metacarpus of the patient. The radius fixing member and the metacarpus fixing member may be connected to each other utilizing a coupling member which may allow the radius fixing member and the metacarpus fixing member to rotate and move linearly in order to provide three degrees of freedom for the exemplary orthopedic device. Furthermore, an exemplary orthopedic device may include a force adjusting mechanism which may be used by a surgeon to exert a controllable tensile force between a radius and a metacarpus of a patient and along an axis perpendicular to a fracture surface.

Figure 1A:
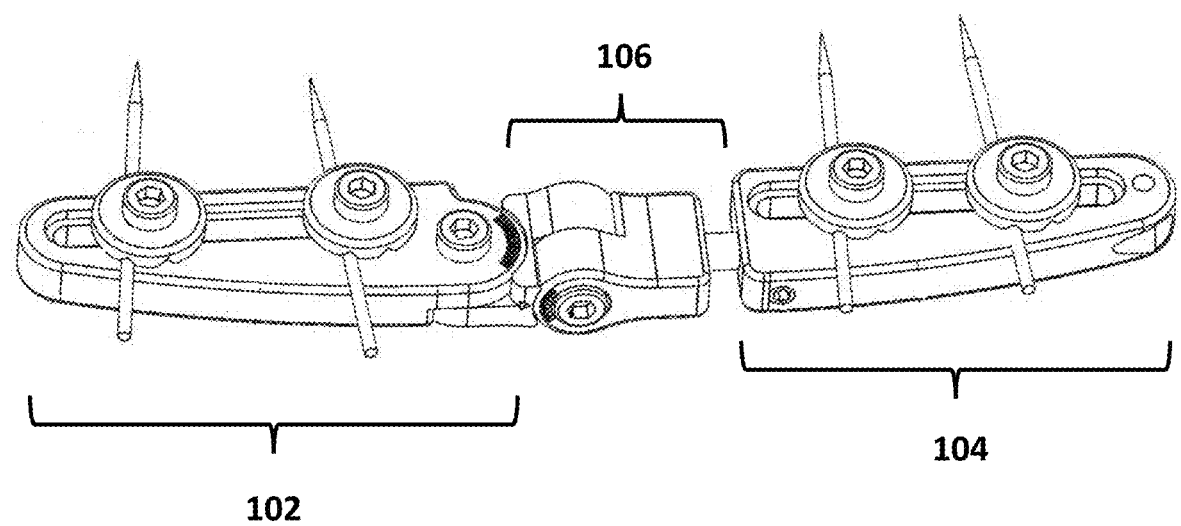
FIG. 1A illustrates a perspective view of an exemplary external orthopedic fixation device, consistent with one or more exemplary embodiments of the present disclosure.
Figure 1B:
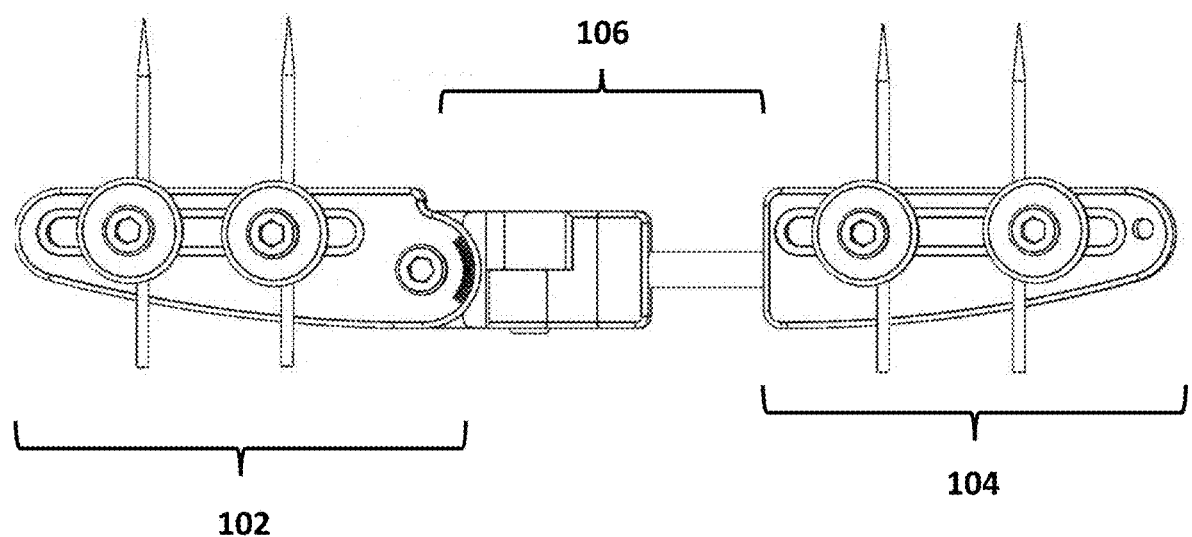
FIG. 1B illustrates a top view of an external orthopedic fixation device, consistent with one or more exemplary embodiments of the present disclosure.
Figure 1C:
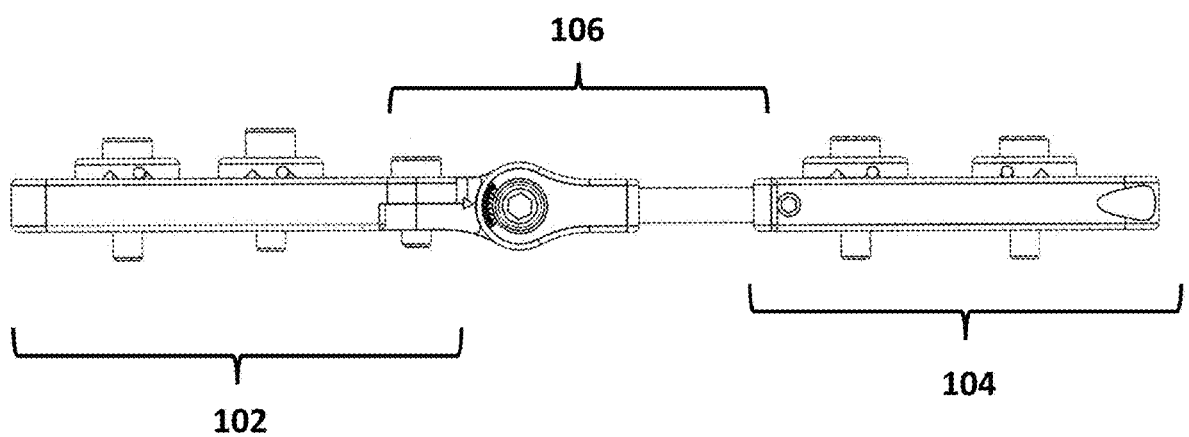
FIG. 1C shows a side view of an external orthopedic fixation device, consistent with one or more exemplary embodiments of the present disclosure.
Figure 1D:
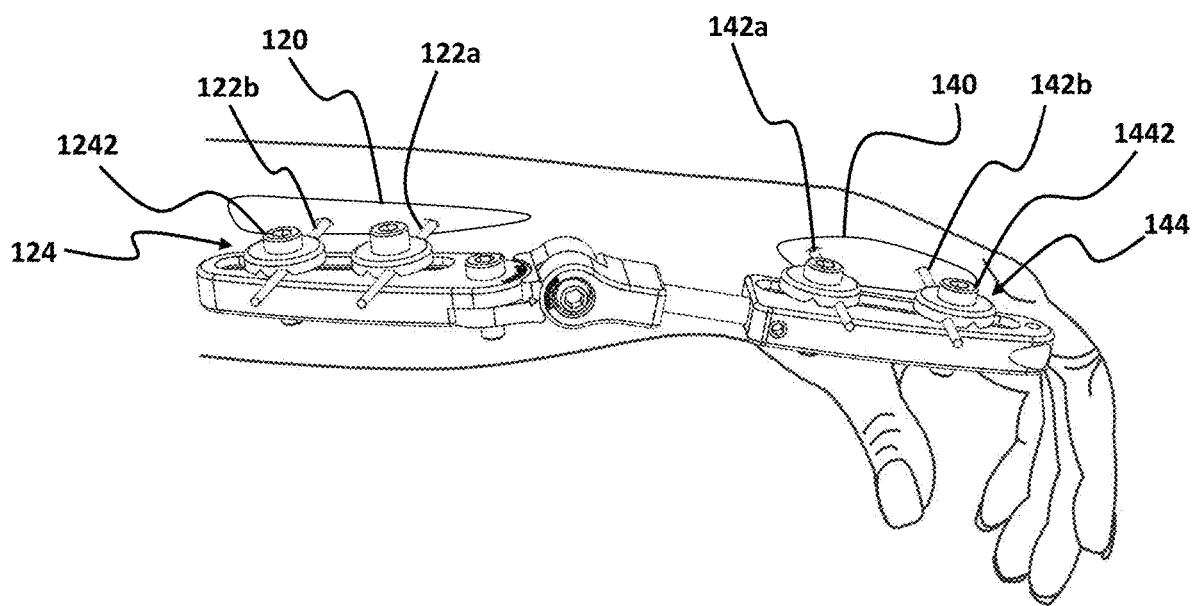
FIG. 1D illustrates an exemplary scenario when external orthopedic fixation device is secured to a hand of a patient, consistent with one or more exemplary embodiments of the present disclosure.

FIG. 1A shows a perspective view of an exemplary external orthopedic fixation device 100, consistent with one or more exemplary embodiments of the present disclosure. FIG. 1B shows a top view of external orthopedic fixation device 100, consistent with one or more exemplary embodiments of the present disclosure. FIG. 1C shows a side view of external orthopedic fixation device 100, consistent with one or more exemplary embodiments of the present disclosure. As shown in FIG. 1A, FIG. 1B, and FIG. 1C, in an exemplary embodiment, external orthopedic fixation device 100 may include a radius fixing member 102 and a metacarpus fixing member 104. FIG. 1D shows an exemplary scenario when external orthopedic fixation device 100 is secured to a hand of a patient, consistent with one or more exemplary embodiments of the present disclosure. As shown in FIG. 1D, in an exemplary embodiment, radius fixing member 102 may be secured to a radius bone 120 of a patient. In an exemplary embodiment, securing radius fixing member 102 to radius bone 120 of the patient may refer to attaching radius fixing member 102 to radius bone 120 in such a way that radius fixing member 102 becomes fixed relative to radius bone 120. In an exemplary embodiment, radius fixing member 102 may be secured to radius fixing member 102 by utilizing a first plurality of bone pins.

In an exemplary embodiment, the first plurality of bone pins may include a first bone pin 122a and a second bone pin 122b. In an exemplary embodiment, a distal end of first bone pin 122a and a distal end of second bone pin 122b may be affixed into radius bone 120. In an exemplary embodiment, a proximal end of first bone pin 122a and a proximal end of second bone pin 122b may be secured to radius fixing member 102. In an exemplary embodiment, the proximal end of second bone pin 122b may be secured to radius fixing member 102 by utilizing a first clamp mechanism 124. In an exemplary embodiment, first clamp mechanism 124 may include a first fastening screw 1242. In an exemplary embodiment, the proximal end of second bone pin 122b may be disposed between first fastening screw 1242 and radius fixing member 102, and by fastening first fastening screw 1242, the proximal end of second bone pin 122b may be secured to radius fixing member 102.

In an exemplary embodiment, metacarpus fixing member 104 may be secured to a metacarpus bone 140 of the patient. In an exemplary embodiment, securing metacarpus fixing member 104 to metacarpus bone 140 of the patient may refer to attaching metacarpus fixing member 104 to metacarpus bone 140 in such a way that metacarpus fixing member 104 is fixed relative to metacarpus bone 140. In an exemplary embodiment, metacarpus fixing member 104 may be secured to metacarpus bone 140 by utilizing a second plurality of bone pins. In an exemplary embodiment, the second plurality of bone pins may include a third bone pin 142a and a fourth bone pin 142b. In an exemplary embodiment, a distal end of third bone pin 142a and a distal end of fourth bone pin 142b may be affixed into metacarpus bone 140. In an exemplary embodiment, a proximal end of third bone pin 142a and a proximal end of fourth bone pin 142b may be secured to metacarpus fixing member 104.

In an exemplary embodiment, the proximal end of fourth bone pin 142b may be secured to metacarpus fixing member 104 by utilizing a second clamp mechanism 144. In an exemplary embodiment, second clamp mechanism 144 may include a second fastening screw 1442. In an exemplary embodiment, the proximal end of second bone pin 142b may be disposed between second fastening screw 1442 and metacarpus fixing member 104, and by fastening second fastening screw 1442, the proximal end of fourth bone pin 142b may be secured to metacarpus fixing member 104. In an exemplary embodiment, external orthopedic fixation device 100 may further include a coupling member 106. In an exemplary embodiment, coupling member 106 may be configured to connect radius fixing member 102 and metacarpus fixing member 104.

Figure 2A:
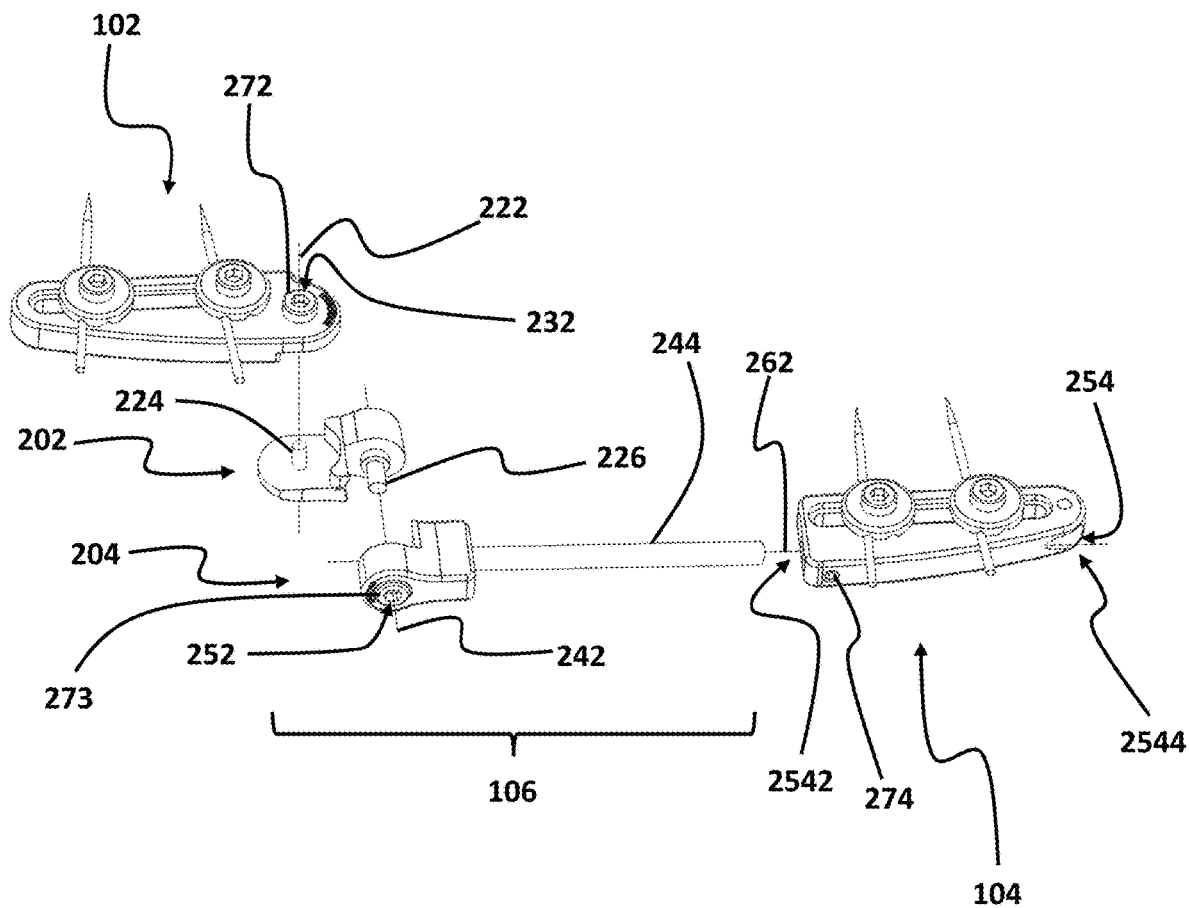
FIG. 2A illustrates an exploded view of an external orthopedic fixation device, consistent with one or more exemplary embodiments of the present disclosure.
Figure 2B:
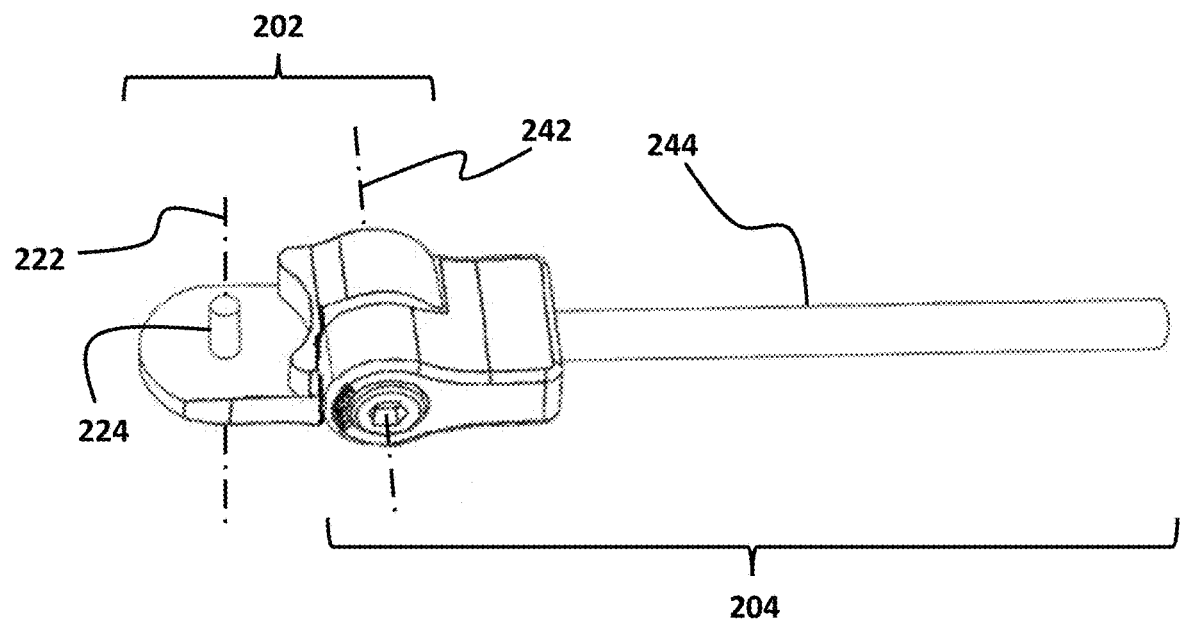
FIG. 2B illustrates a perspective view of a coupling member, consistent with one or more exemplary embodiments of the present disclosure.

FIG. 2A shows an exploded view of external orthopedic fixation device 100, consistent with one or more exemplary embodiments of the present disclosure. FIG. 2B shows a perspective view of coupling member 106, consistent with one or more exemplary embodiments of the present disclosure. As shown in FIG. 2A and FIG. 2B, in an exemplary embodiment, coupling member 106 may include a radius coupling element 202. In an exemplary embodiment, radius coupling element 202 may be connected to radius fixing member 102 in such a way that radius coupling element 202 be able to rotate around a first axis 222. In an exemplary embodiment, first axis 222 may be associated with radius fixing member 102. In fact, in an exemplary embodiment, first axis 222 may be fixed to radius fixing member 102. In an exemplary embodiment, radius coupling element 202 may include a first attaching rod 224. In an exemplary embodiment, first attaching rod 224 may be disposed freely inside a first rod receiving hole 232 of radius fixing member 102. In an exemplary embodiment, disposing first attaching rod 224 freely inside first rod receiving hole 232 may refer to an exemplary scenario in which an external diameter of first attaching rod 224 is smaller than an internal diameter of first rod receiving hole 232. In an exemplary embodiment, the difference between the external diameter of first attaching rod 224 and the internal diameter of first rod receiving hole 232 may allow first attaching rod 224 to rotate freely inside first rod receiving hole 232.

In an exemplary embodiment, as shown in FIG. 2A and FIG. 2B, coupling member 106 may further include a metacarpus coupling element 204. In an exemplary embodiment, metacarpus coupling element 204 may be connected to radius coupling element 202 in such a way that metacarpus coupling element 204 may be able to rotate around a second axis 242. In an exemplary embodiment, second axis 242 may be associated with radius coupling element 202. In an exemplary embodiment, radius coupling element 202 may include a second attaching rod 226. In an exemplary embodiment, second attaching rod 226 may be disposed freely inside a second rod receiving hole 252 of metacarpus coupling element 204. In an exemplary embodiment, disposing second attaching rod 226 freely inside second rod receiving hole 252 may refer to an exemplary scenario in which an external diameter of second attaching rod 226 is smaller than an internal diameter of second rod receiving hole 252. In an exemplary embodiment, the difference between the external diameter of second attaching rod 226 and the internal diameter of second rod receiving hole 252 may allow second attaching rod 226 to rotate freely inside rod receiving hole 232.

In an exemplary embodiment, coupling member 106 may further include a first locking nut 272 associated with first attaching rod 224. In an exemplary embodiment, first attaching rod 224 may include a first externally threaded section corresponds to a first internally threaded section of first locking nut 272. In an exemplary embodiment, first locking nut 272 and first attaching rod 224 may act as a nut and screw mechanism. In an exemplary embodiment, responsive to fastening first locking nut 272, radius coupling element 202 may be prevented from rotating around first axis 222 and, consequently, radius coupling element 202 may be fixed relative to radius fixing member 102.

In an exemplary embodiment, coupling member 106 may further include a second locking nut 273 associated with second attaching rod 226. In an exemplary embodiment, second attaching rod 226 may include a second externally threaded section corresponds to a second internally threaded section of second locking nut 273. In an exemplary embodiment, second locking nut 273 and second attaching rod 226 may act as a nut and screw mechanism. In an exemplary embodiment, responsive to fastening second locking nut 272, metacarpus coupling element 204 may be prevented from rotating around second axis 222 and, consequently, metacarpus coupling element 204 may be fixed relative to radius coupling element 202.

In an exemplary embodiment, metacarpus coupling element 204 may further include a first adjusting rod 244. In an exemplary embodiment, first adjusting rod 244 may be disposed slidably inside an adjusting hole 254 of metacarpus fixing member 104 from a first side 2542 of adjusting hole 254. In an exemplary embodiment, disposing first adjusting rod 244 slidably inside adjusting hole 254 may refer to disposing first adjusting rod 244 inside adjusting hole 254 in such a way that first adjusting rod 244 is able to move linearly inside adjusting hole 254 and along a third axis 262. In an exemplary embodiment, third axis 262 may be associated with metacarpus fixing member 104. In an exemplary embodiment, third axis 262 may be the same as a main longitudinal axis of adjusting hole 254. In an exemplary embodiment, disposing first adjusting rod 244 slidably inside adjusting hole 254 may allow metacarpus fixing member 104 to move linearly along third axis 262 and relative to coupling member 106.

In an exemplary embodiment, coupling member 106 may further include a locking screw 274 associated with first adjusting rod 244. In an exemplary embodiment, due to fastening locking screw 274, first adjusting rod 244 may be prevented from linear movement along third axis 262 and, in fact, metacarpus coupling element 204 may be fixed relative to metacarpus fixing member 104.

Figure 3A:
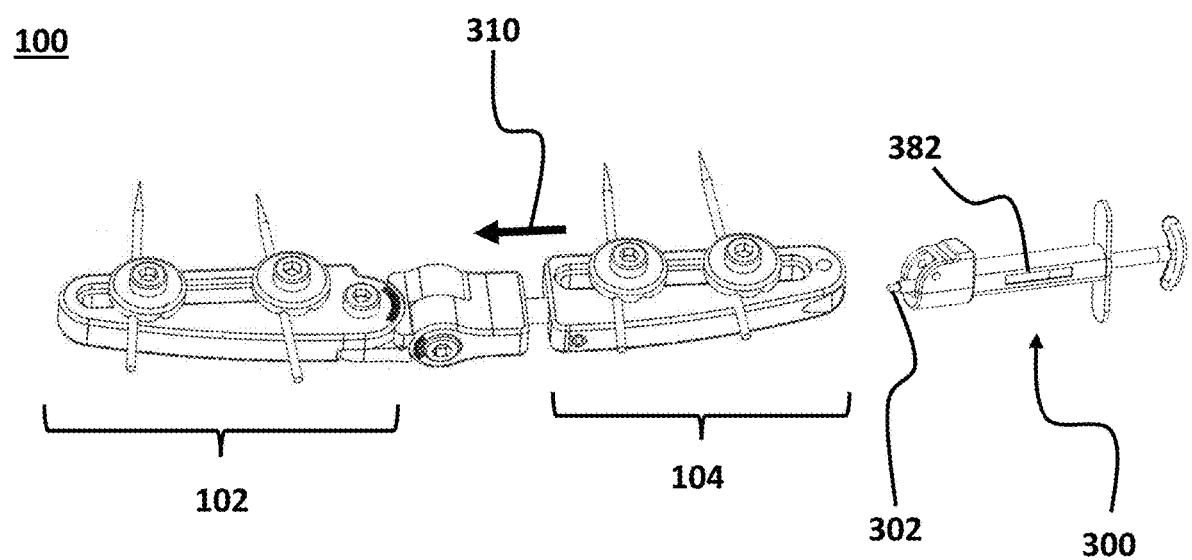
FIG. 3A illustrates an external orthopedic fixation device, consistent with one or more exemplary embodiments of the present disclosure.
Figure 3B:
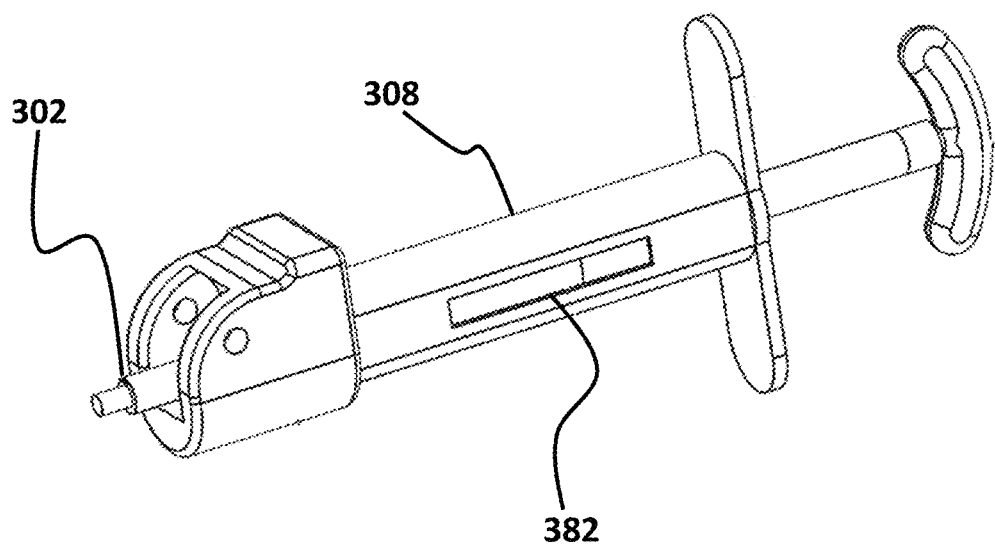
FIG. 3B illustrates a force adjusting mechanism, consistent with one or more exemplary embodiments of the present disclosure.

FIG. 3A shows external orthopedic fixation device 100, consistent with one or more exemplary embodiments of the present disclosure. As shown in FIG. 3A, in an exemplary embodiment, external orthopedic fixation device 100 may further include a force adjusting mechanism 300. In an exemplary embodiment, force adjusting mechanism 300 may be configured to exert a tensile force between radius fixing member 102 and metacarpus fixing member 104. FIG. 3B shows force adjusting mechanism 300, consistent with one or more exemplary embodiments of the present disclosure. In an exemplary embodiment, force adjusting mechanism 300 may include a second adjusting rod 302.

In an exemplary embodiment, second adjusting rod 302 may be configured to be inserted inside a second side 2544 of adjusting hole 254 and urge first adjusting rod 244 to move linearly inside adjusting hole 254 and along third axis 262. In an exemplary embodiment, second adjusting rod 302 may urge first adjusting rod 244 to move along third axis 262 and in a direction 310. In an exemplary embodiment, moving first adjusting rod 244 inside adjusting hole 254 and in direction 310 may increase a distance between radius fixing member 102 and metacarpus fixing member 104. Furthermore, in an exemplary embodiment, moving first adjusting rod 244 inside adjusting hole 254 and in direction 310 may exert a tensile force between radius fixing member 102 and metacarpus fixing member 104. In an exemplary embodiment, it may be understood that the tensile force between radius fixing member 102 and metacarpus fixing member 104 may directly be applied between radius bone 120 and metacarpus bone 140.

Figure 3C:
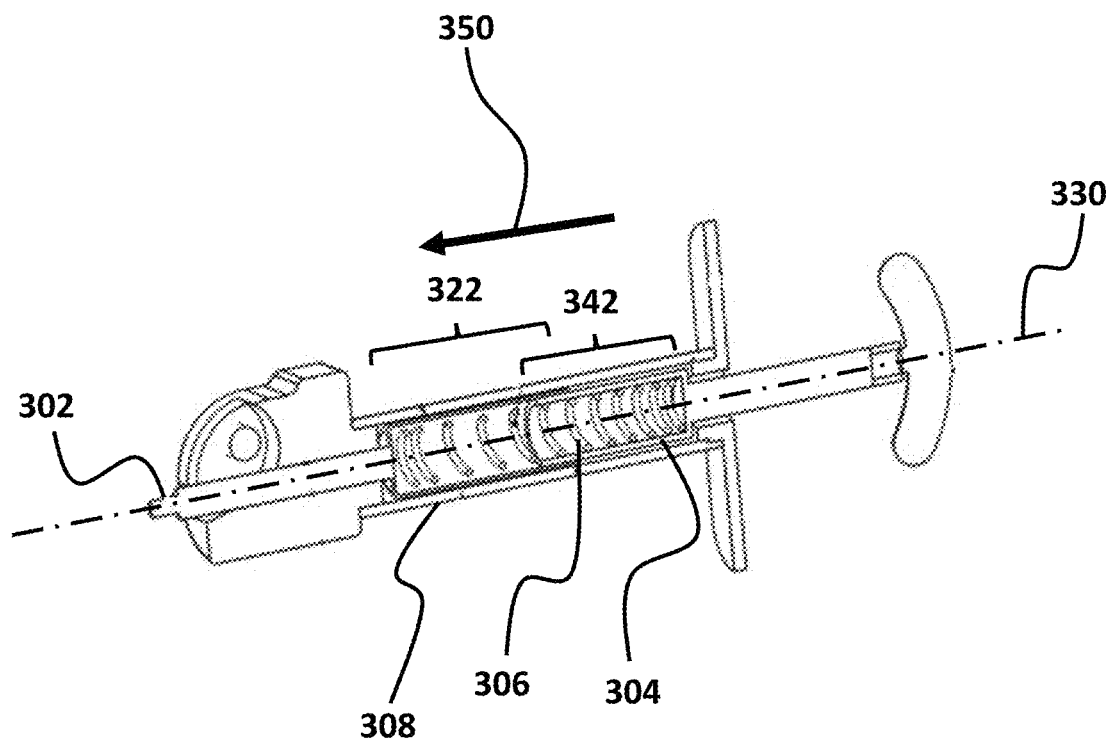
FIG. 3C illustrates a sectional view of a force adjusting mechanism, consistent with one or more exemplary embodiments of the present disclosure.
Figure 3D:
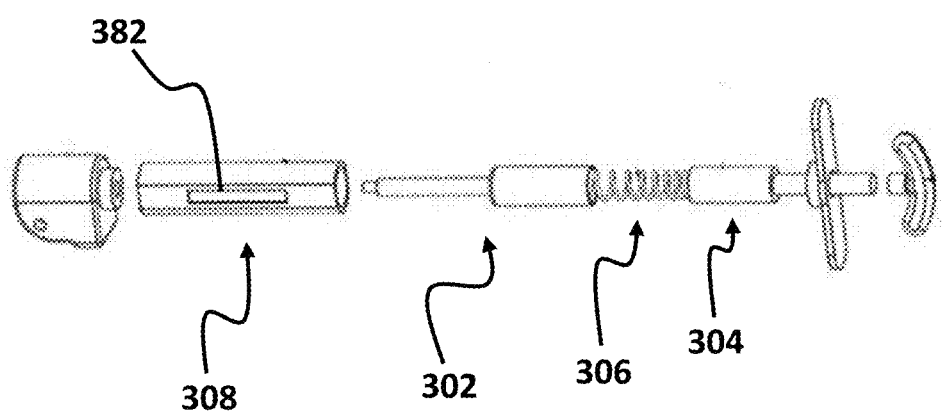
FIG. 3D illustrates an exploded view of a force adjusting mechanism, consistent with one or more exemplary embodiments of the present disclosure.
Figure 3E:
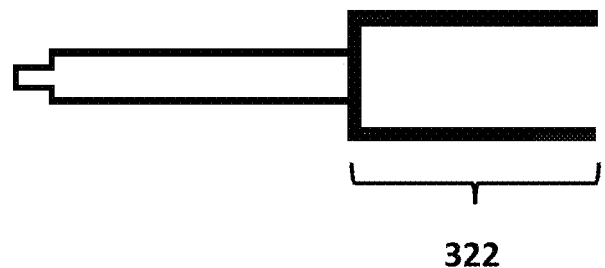
FIG. 3E illustrates a sectional view of a second adjusting rod, consistent with one or more exemplary embodiments of the present disclosure.
Figure 3F:
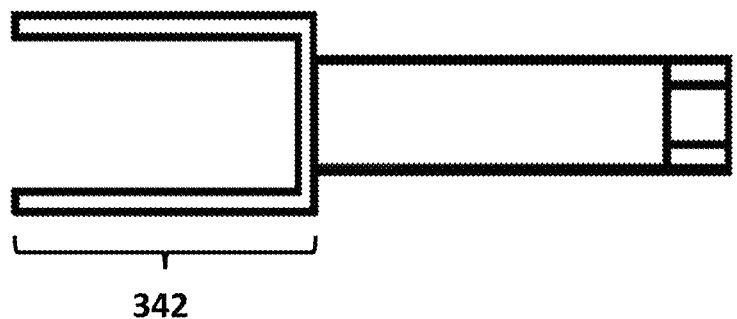
FIG. 3F illustrates a sectional view of a pushing member, consistent with one or more exemplary embodiments of the present disclosure.

FIG. 3C shows a sectional view of force adjusting mechanism 300, consistent with one or more exemplary embodiments of the present disclosure. FIG. 3D shows an exploded view of force adjusting mechanism 300, consistent with one or more exemplary embodiments of the present disclosure. As shown in FIG. 3C and FIG. 3D, in an exemplary embodiment, force adjusting mechanism 300 may further include a pushing member 304 and a spring 306. FIG. 3E shows a sectional view of second adjusting rod 302, consistent with one or more exemplary embodiments of the present disclosure. FIG. 3F shows a sectional view of pushing member 304, consistent with one or more exemplary embodiments of the present disclosure.

Referring back to FIG. 3C, in an exemplary embodiment, a first hollow cylindrical section 342 of pushing member 304 may be disposed slidably inside a second hollow cylindrical section 322 of second adjusting rod 302. Furthermore, spring 306 may be disposed between second adjusting rod 302 and pushing member 304 and inside first hollow cylindrical section 342 and second hollow cylindrical section 322. In an exemplary embodiment, when pushing member 304 is moved along a fourth axis 330 and in a direction 350, it may compress spring 306, and to thereby, may urge second adjusting rod 302 to move along fourth axis 330 and in direction 350. In an exemplary embodiment, force adjusting mechanism 300 may further include a shell 308. In an exemplary embodiment, second adjusting rod 302 and pushing member 304 may be disposed slidably inside shell 308. In an exemplary embodiment, shell 308 may include a slot 382.

In an exemplary embodiment, slot 382 may provide a facility for a surgeon to see the amounts which second adjusting rod 302 and pushing member 304 are moved along fourth axis 330 and in direction 350. In an exemplary embodiment, a difference between an amount which pushing member 304 is moved along fourth axis 330 and in direction 350 and an amount which second adjusting rod 302 is moved along fourth axis 330 and in direction 350 may be the same as an amount which spring 306 is compressed. In an exemplary embodiment, it may be understood that the amount which spring 306 is compressed may be an indication for the tensile force between radius fixing member 102 and metacarpus fixing member 104. Consequently, in an exemplary embodiment, slot 382 may act as a force indicator which provide a facility for a surgeon to calculate the tensile force between radius fixing member 102 and metacarpus fixing member 104.

In an exemplary embodiment, it may be understood that the tensile force between radius fixing member 102 and metacarpus fixing member 104 may be a force along third axis 262. In an exemplary embodiment, a tensile force along third axis 262 may refer to a force which is able to pull radius fixing member 102 in direction of third axis 262. A surgeon may rotate metacarpus fixing member 104 around first axis 222 and second axis 242 to change a direction of third axis 262 in space. For example, a surgeon may rotate metacarpus fixing member 104 around first axis 222 and second axis 242 to set third axis 262 along an axis perpendicular to a fracture plane or a distal radius articular plane. Consequently, the tensile force between radius fixing member 102 and metacarpus fixing member 104 which may be applied between radius bone 120 and metacarpus bone 140 may be a tensile force along the axis perpendicular to the fracture plane or the distal radius articular plane.

Figure 3G:
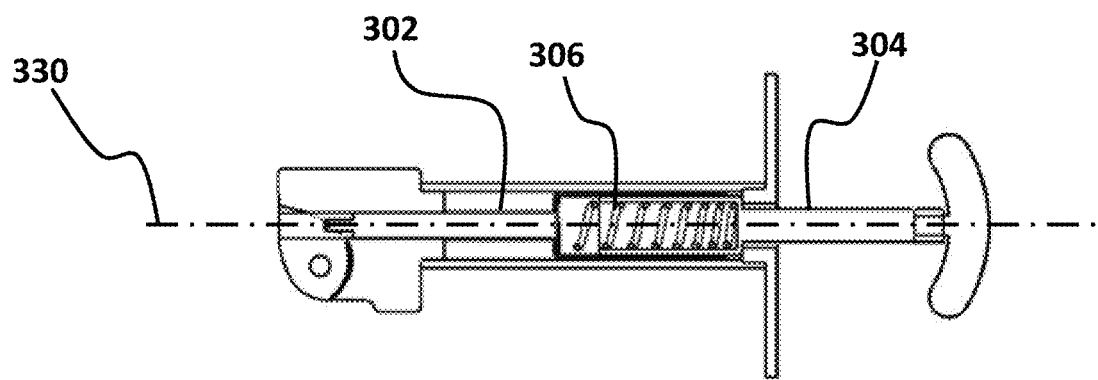
FIG. 3G illustrates a side view of an adjusting mechanism in a scenario when pushing member is free and not moved along fourth axis.
Figure 3H:
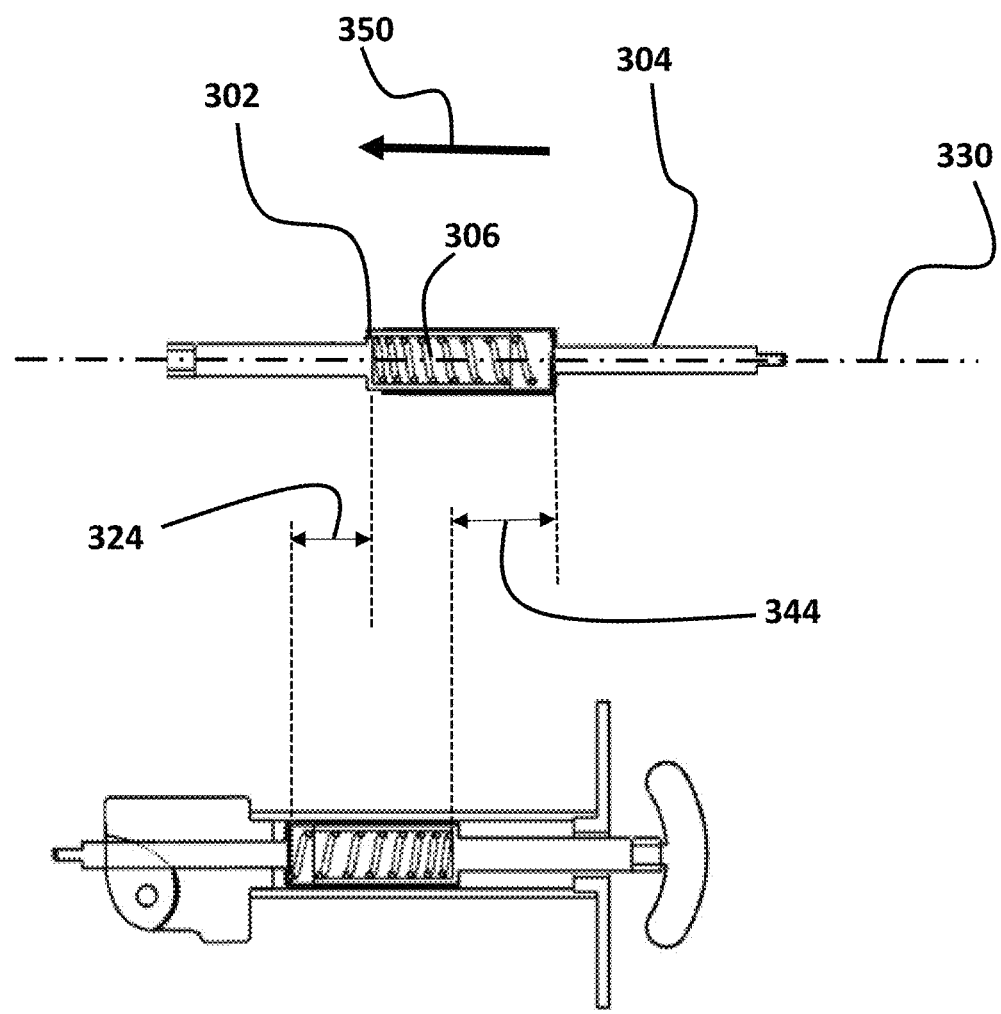
FIG. 3H illustrates a side view of an adjusting mechanism in a scenario when pushing member is moved along fourth axis, consistent with one or more exemplary embodiments of the present disclosure.

FIG. 3G shows a side view of adjusting mechanism 300 in a scenario when pushing member 304 is free and not moved along fourth axis 330. FIG. 3H shows a side view of adjusting mechanism 300 in a scenario when pushing member 304 is moved along fourth axis 330 and in direction 350, consistent with one or more exemplary embodiments of the present disclosure. As may be seen in FIG. 3G, in an exemplary embodiment, when pushing member 304 is moved along fourth axis 330 and in direction 350, pushing member 304 may be moved by a first amount 344 and second adjusting rod 302 may be moved by a second amount 324. In an exemplary embodiment, it may be understood that a difference between first amount 344 and second amount 324 may be equal to a compression amount of spring 306. Furthermore, it may be understood that a surgeon, utilizing a compression amount of spring 306, may be able to calculate a tensile force applied by external orthopedic fixation device 100 between radius bone 120 and metacarpus bone 140. Hence, disclosed external orthopedic fixation device 100 may provide a facility for a surgeon to make him/her able to exert a controllable tensile force between a radius bone of a patient and a metacarpus bone of a patient. In an exemplary embodiment, exerting a controllable tensile force may refer to exerting a tensile force in a predetermined direction and by a predetermined magnitude.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. An external orthopedic fixation device, comprising:
a radius fixing member configured to be secured to a radius bone of a patient;
a metacarpus fixing member configured to be secured to a metacarpus bone of the patient, the metacarpus fixing member comprising an adjusting hole; and
a coupling member disposed between the radius fixing member and the metacarpus fixing member, the coupling member configured to connect the radius fixing member and the metacarpus fixing member, the coupling member comprising:
a radius coupling element connected to the radius fixing member, the radius coupling element configured to rotate around a first axis, the first axis fixed to the radius fixing member;
a metacarpus coupling element disposed between the metacarpus fixing member and the radius coupling element, the metacarpus coupling element connected to the metacarpus fixing member and the radius coupling element, the metacarpus coupling element configured to rotate around a second axis, the second axis fixed to the radius coupling element, the metacarpus coupling element comprising a first adjusting rod associated with the adjusting hole, the first adjusting rod disposed slidably inside a first side of the adjusting hole, a distance between the radius fixing member and the metacarpus fixing member configured to be changed responsive to linear movement of the first adjusting rod inside the adjusting hole and along a third axis; and
a force adjusting mechanism configured to exert a tensile force between the radius fixing member and the metacarpus fixing member through urging the first adjusting rod to move linearly inside the adjusting hole and along the third axis, the force adjusting mechanism comprising:
a second adjusting rod comprising a second hollow cylindrical section, the second adjusting rod configured to:
be inserted inside a second side of the adjusting hole; and
urge the first adjusting rod to move linearly inside the adjusting hole and along the third axis;
a pushing member comprising a first hollow cylindrical section, the first hollow cylindrical section disposed slidably inside the second hollow cylindrical section; and
a spring disposed between the second adjusting rod and the pushing member, the spring disposed inside the first hollow cylindrical section and the second hollow cylindrical section, responsive to linear movement of the pushing member inside the second hollow cylindrical section and along a fourth axis, the spring configured to compress, and to thereby, urge the second adjusting rod to move along the fourth axis,
wherein the coupling member is configured to allow rotational movements of the radius fixing member around the first axis and the second axis.

2. The external orthopedic fixation device of claim 1, wherein the force adjusting mechanism further comprises a shell, the second adjusting rod and the pushing member disposed slidably inside the shell, responsive to linear movement of the first hollow cylindrical section of pushing member inside the second hollow cylindrical section and along the fourth axis, the spring is configured to compress, and to thereby urge the second adjusting rod to move along the fourth axis and inside the shell.

3. The external orthopedic fixation device of claim 2, wherein the first axis is perpendicular to the second axis.

4. The external orthopedic fixation device of claim 3, wherein the second axis is perpendicular to the third axis.

5. The external orthopedic fixation device of claim 4, wherein the fourth axis is the same as the third axis.

6. The external orthopedic device of claim 5, wherein the shell comprises a slot on an outermost surface of the shell, the slot configured to provide a view of the pushing member and the second adjusting rod to a surgeon.

7. The external orthopedic device of claim 6, wherein the coupling member further comprises:
a first locking nut, a first internally threaded section of the first locking nut corresponding to a first externally threaded section of a first attaching rod, the first internally threaded section of the first locking nut configured to be meshed with the first externally threaded section of the first attaching rod, responsive to fastening the first locking nut onto the first attaching rod, the radius coupling element configured to be prevented from rotating around the first axis and, to thereby, radius coupling element be fixed relative to radius fixing member; and
a second locking nut, a second internally threaded section of the second locking nut corresponding to a second externally threaded section of a second attaching rod, the second internally threaded section of the second locking nut configured to be meshed with the second externally threaded section of the second attaching rod, responsive to fastening the second locking nut onto the second attaching rod, the metacarpus coupling element configured to be prevented from rotating around the second axis and, to thereby, metacarpus coupling element be fixed relative to radius coupling element.

8. The external orthopedic device of claim 7, wherein the coupling member further comprises a locking screw associated with the first adjusting rod, responsive to fastening the locking screw, a friction between the locking screw and the first adjusting rod is configured to be increased, and to thereby, prevent first adjusting rod from linear movement along the third axis, and to thereby, fix the metacarpus coupling element relative to metacarpus fixing member.

9. An external orthopedic fixation device, comprising:
a radius fixing member configured to be secured to a radius bone of a patient;
a metacarpus fixing member configured to be secured to a metacarpus bone of the patient, the metacarpus fixing member comprising an adjusting hole;
a radius coupling element connected to the radius fixing member;
a metacarpus coupling element interconnected between the metacarpus fixing member and the radius coupling element, the metacarpus coupling element comprising a first adjusting rod, the first adjusting rod disposed slidably inside a first side of the adjusting hole, a distance between the radius fixing member and the metacarpus fixing member configured to be changed responsive to linear movement of the first adjusting rod inside the adjusting hole; and
a force adjusting mechanism configured to exert a tensile force between the radius fixing member and the metacarpus fixing member through urging the first adjusting rod to move linearly inside the adjusting hole, the force adjusting mechanism comprising:

a second adjusting rod comprising a second hollow cylindrical section, the second adjusting rod configured to:
be inserted inside a second side of the adjusting hole; and
urge the first adjusting rod to move linearly inside the adjusting hole;
a pushing member comprising a first hollow cylindrical section, the first hollow cylindrical section disposed slidably inside the second hollow cylindrical section; and
a spring disposed between the second adjusting rod and the pushing member, the spring disposed inside the first hollow cylindrical section and the second hollow cylindrical section, responsive to linear movement of the pushing member inside the second hollow cylindrical section, the spring configured to compress, and to thereby, urge the second adjusting rod to move.

10. The external orthopedic fixation device of claim 9, wherein the force adjusting mechanism further comprises a shell, the second adjusting rod and the pushing member disposed slidably inside the shell, responsive to linear movement of the first hollow cylindrical section of pushing member inside the second hollow cylindrical section and along a fourth axis, the spring is configured to compress, and to thereby urge the second adjusting rod to move along the fourth axis and inside the shell.

11. The external orthopedic device of claim 10, wherein the shell comprises a slot on an outermost surface of the shell, the slot configured to provide a view of the pushing member and the second adjusting rod to a surgeon.

12. The external orthopedic device of claim 11, wherein the coupling member further comprises:
a first locking nut, a first internally threaded section of the first locking nut corresponding to a first externally threaded section of a first attaching rod, the first internally threaded section of the first locking nut configured to be meshed with the first externally threaded section of the first attaching rod, responsive to fastening the first locking nut onto the first attaching rod, the radius coupling element configured to be prevented from rotating around a first axis and, to thereby, radius coupling element be fixed relative to radius fixing member; and
a second locking nut, a second internally threaded section of the second locking nut corresponding to a second externally threaded section of a second attaching rod, the second internally threaded section of the second locking nut configured to be meshed with the second externally threaded section of the second attaching rod, responsive to fastening the second locking nut onto the second attaching rod, the metacarpus coupling element configured to be prevented from rotating around a second axis and, to thereby, metacarpus coupling element be fixed relative to radius coupling element.

13. The external orthopedic device of claim 12, wherein the coupling member further comprises a locking screw associated with the first adjusting rod, responsive to fastening the locking screw, a friction between the locking screw and the first adjusting rod is configured to be increased, and to thereby, prevent first adjusting rod from linear movement along a third axis, and to thereby, fix the metacarpus coupling element relative to metacarpus fixing member.

14. The external orthopedic fixation device of claim 13, wherein:
the first axis is perpendicular to the second axis;
the second axis is perpendicular to the third axis; and
the fourth axis is the same as the third axis.

* * * * *